(12) United States Patent
Kobayashi et al.

(10) Patent No.: US 8,709,339 B2
(45) Date of Patent: Apr. 29, 2014

(54) APPARATUS AND METHOD FOR STERILIZING VESSEL WITH ELECTRON BEAM

(71) Applicants: Toshiya Kobayashi, Tokyo (JP); Mitsuomi Narita, Aichi (JP); Tomohiko Sugimori, Urayasu (JP); Tsunehiko Yokoi, Shanghai (JP); Yukinobu Nishino, Kanazawa (JP); Masami Hayashi, Kanazawa (JP); Hideki Nishikawa, Kanazawa (JP); Yukihiro Yamamoto, Kanazawa (JP); Tokuo Nishi, Kanazawa (JP)

(72) Inventors: Toshiya Kobayashi, Tokyo (JP); Mitsuomi Narita, Aichi (JP); Tomohiko Sugimori, Urayasu (JP); Tsunehiko Yokoi, Shanghai (JP); Yukinobu Nishino, Kanazawa (JP); Masami Hayashi, Kanazawa (JP); Hideki Nishikawa, Kanazawa (JP); Yukihiro Yamamoto, Kanazawa (JP); Tokuo Nishi, Kanazawa (JP)

(73) Assignee: Shibuya Kogyo Co., Ltd., Kanazawa-shi, Ishikawa (JP)

( * ) Notice: Subject to any disclaimer, the term of this patent is extended or adjusted under 35 U.S.C. 154(b) by 0 days.

(21) Appl. No.: 13/788,205

(22) Filed: Mar. 7, 2013

(65) Prior Publication Data
US 2013/0202481 A1 Aug. 8, 2013

Related U.S. Application Data

(62) Division of application No. 12/657,491, filed on Jan. 21, 2010, now Pat. No. 8,415,645.

(30) Foreign Application Priority Data

Jan. 22, 2009 (JP) .................................. 2009-02306
Jun. 30, 2009 (JP) .................................. 2009-156097

(51) Int. Cl.
| | | |
|---|---|---|
| A61L 2/00 | (2006.01) | |
| G01N 23/00 | (2006.01) | |
| A01N 1/02 | (2006.01) | |
| A61K 41/00 | (2006.01) | |
| A61L 9/22 | (2006.01) | |

(52) U.S. Cl.
CPC ............... *A01N 1/0294* (2013.01); *A61K 41/00* (2013.01); *A61L 9/22* (2013.01); *A61L 2/00* (2013.01)
USPC .................. 422/22; 422/186.05; 250/455.11; 250/492.1; 250/492.3

(58) Field of Classification Search
CPC .......... A01N 1/0294; A61L 2/00; A61L 9/22; A61K 41/00
USPC .................. 422/6, 14, 22–23, 28, 33, 186.05, 422/186.29, 186.3, 305; 250/455.11, 492.1, 250/492.3; 204/157.44, 193; 315/111.81; 313/107.5
See application file for complete search history.

(56) References Cited

U.S. PATENT DOCUMENTS

2010/0123090 A1  5/2010 Nishino et al.

FOREIGN PATENT DOCUMENTS

| JP | 09-150813 | 6/1997 |
| JP | 2004-014319 | * 1/2004 |
| JP | 2008-296955 | 12/2008 |

OTHER PUBLICATIONS

Japaneses Patent Office machine English translation of the "Detailed section" of JP 2004-014319.*
Japaneses Patent Office machine English translation of the "Detailed section" of JP 406183893 A.*
Japanese Office Action dated Jul. 2, 2013 with English translation thereof (9 pages).

* cited by examiner

*Primary Examiner* — Monzer R Chorbaji

(74) *Attorney, Agent, or Firm* — Flynn, Thiel, Boutell & Tanis, P.C.

(57) ABSTRACT

To prevent electrical charging inside a resin material as well as a surface of a resin vessel at a time of sterilizing the resin vessel by being irradiated with electron beam, a bottle support unit is mounted to a lower end portion of a cylindrical rotating shaft rotatably supported by a rotating wheel. The bottle support unit includes a pair of griper members by which a mouth portion of a bottle is gripped. A ground electrode is disposed to be capable of being inserted into the interior of the resin vessel through a mouth portion thereof, and the interior of the resin vessel is irradiated with the electron beam in a state of the ground electrode being inserted into the resin vessel.

4 Claims, 7 Drawing Sheets

APPARATUS AND METHOD FOR STERILIZING VESSEL WITH ELECTRON BEAM

This is a divisional of prior U.S. application Ser. No. 12/657,491, filed Jan. 21, 2010.

FIELD OF THE INVENTION

The present invention relates to an apparatus for and a method of irradiating resin vessels with an electron beam to thereby sterilize the vessels, and more particularly, to an electron beam irradiation vessel sterilization apparatus and an electron beam irradiation vessel sterilization method capable of preventing a resin vessel from being electrically charged by the irradiation with the electron beam. This electron beam irradiation vessel sterilization apparatus of the present invention may be simply called hereinlater as "electron beam sterilizer".

BACKGROUND OF THE INVENTION

Apparatus for irradiating resin vessels such as PET bottles with an electron beam for sterilizing the same have been widely known in conventional technology. It is also conventionally known that the resin vessel is electrostatically charged by being irradiated with the electron beam for sterilizing the vessel (for example, refer to Japanese Patent Application Laid-open Publication No. 2007-126171: Patent Publication 1).

This Patent Publication 1 discloses a PET bottle drink filling system having a structure in which the PET bottle entering from an entrance port is conveyed to a sterilization section by a food vessel conveying device, and then, is sterilized by being irradiated with the electron beam from an electron beam irradiating device. The sterilized PET bottle is then conveyed to a wash-out rinser so as to be cleaned by water or air. The PET bottle discharged out of the rinser is filled up with inner content by a filling device. The PET bottle filled up with the inner content is then applied with a cap by a capper so as to seal the PET bottle.

With the structure disclosed in the above Patent Publication 1, since the PET bottle is electrostatically charged with the irradiation from the electron beam, it is necessary to arrange a charge amount measuring device for detecting the charge amount, and the measured charge amount is sent to a computer from the charge amount measuring device to analyze the charge amount so as to judge whether the charge amount of the PET bottle generated by the irradiation with the electron beam is within a predetermined range or out of range.

If the resin bottle is electrostatically charged, dirt or dust may be attracted thereto, thus arising an inconvenient matter. Then, various apparatus or devices have been conventionally proposed to remove the static electricity charging the resin vessels (for example, refer to Japanese Patent Application Laid-open Publication Nos. 2000-68093 and 2004-14319: Patent Publications 2 and 3).

In the invention concerning a static electricity removing method and apparatus disclosed in the above Patent Publication 2, the static electricity is removed by irradiating a resin hollow vessel with an X-ray. Further, in the invention concerning a static electricity removing apparatus disclosed in the above Patent Publication 3, a loop nozzle curved in form of loop and formed with an air discharging port is provided for discharging air against an outer surface of a bottle and a straight nozzle formed with another air discharging port for discharging air against an inner surface of the bottle, and by blowing ionized air from these nozzles to the outer and inner surfaces of the bottle, the static electricity charged on these surfaces is thereby removed.

It may be possible to reduce the charging on the inner and outer surfaces of the resin vessel (bottle) by removing the static electricity by the method and/or apparatus disclosed in the Patent Publications 2 and 3. However, even by these methods and apparatus, it was difficult to remove the charge accumulated inside the resin material (substance) itself forming the bottle.

SUMMARY OF THE INVENTION

The present invention was conceived in consideration of the circumstances encountered in the prior art mentioned above and an object thereof is to provide an apparatus and a method for sterilizing a vessel with electron beam irradiation, i.e., an electron beam sterilizer, capable of preventing a charge which may be caused inside a resin material forming the vessel as well as removing charges stuck on inner and outer surfaces of the vessel.

The above and other objects can be achieved by providing, in one aspect of the present invention, an electron beam sterilizer for sterilizing a resin vessel by irradiating the resin vessel with an electron beam emitted from an electron beam irradiator, wherein the electron beam sterilizer is provided with a ground electrode to be inserted into the resin vessel through an opening thereof, and the resin vessel is irradiated with the electron beam in a state in which the ground electrode is inserted into the resin vessel.

According to the above aspects and preferred embodiments of the present invention, the ground electrode is inserted into the resin vessel at the time of sterilizing the resin vessel with the electron beam, so that the resin vessel can be prevented from being electrically charged.

In another aspect of the present invention, the above object can be also achieved by providing an electron beam sterilization method for sterilizing a resin vessel by irradiating the resin vessel with an electron beam emitted from an electron beam irradiator, the method being characterized by inserting a ground electrode into an interior of the resin vessel through an opening thereof and, in this state, irradiating the resin vessel with the electron beam.

In preferred embodiments of the above aspects, the ground electrode may be formed with a gas passage, and when the ground electrode is inserted into the resin vessel to be irradiated with the electron beam, an aseptic gas blows into the resin vessel through the gas passage.

According to the irradiation with the electron beam while blowing the aseptic gas into the resin vessel, ozone generated by the electron beam irradiation can be pushed out and hence removed from the resin vessel as well as dust, dirt and the like, thus achieving air-rinsing effect. Especially, if inactive gas is utilized as aseptic gas, since the oxygen density in the resin vessel is reduced, the generation of the ozone can be further prevented. In addition, the use of the aseptic gas does not give inferior effect to the sterilization performance. Furthermore, the apparatus may be provided with an ionizer for blowing out the ionized aseptic gas and, in such a case, the electrical charging on the inner surface of the resin vessel can be further prevented in addition to the function of the location of the ground electrode.

In a further aspect of the present invention, there is also provided an electron beam sterilizer for sterilizing a resin vessel by irradiating the resin vessel with an electron beam emitted from an electron beam irradiator, wherein the electron beam sterilizer is provided with an insertion member to be inserted into the resin vessel through an opening thereof, the insertion member having a positive potential, and the resin vessel is irradiated with the electron beam in a state in which the insertion member is inserted into the resin vessel.

In further aspects of the present invention, the insertion member may be further provided so as to be connected to an anode to which a positive voltage is applied, so that the resin vessel can be prevented from being electrically charged.

BRIEF DESCRIPTION OF THE DRAWINGS

In the accompanying drawings:

FIGS. 6A and 6B are a view showing an essential portion of an electron beam irradiation vessel sterilization apparatus (electron beam sterilizer) according to a third embodiment, in which FIGS. 6A and 6B show states corresponding to FIGS. 2A and 2B, respectively.

DESCRIPTION OF THE PREFERRED EMBODIMENTS

Figure 1:
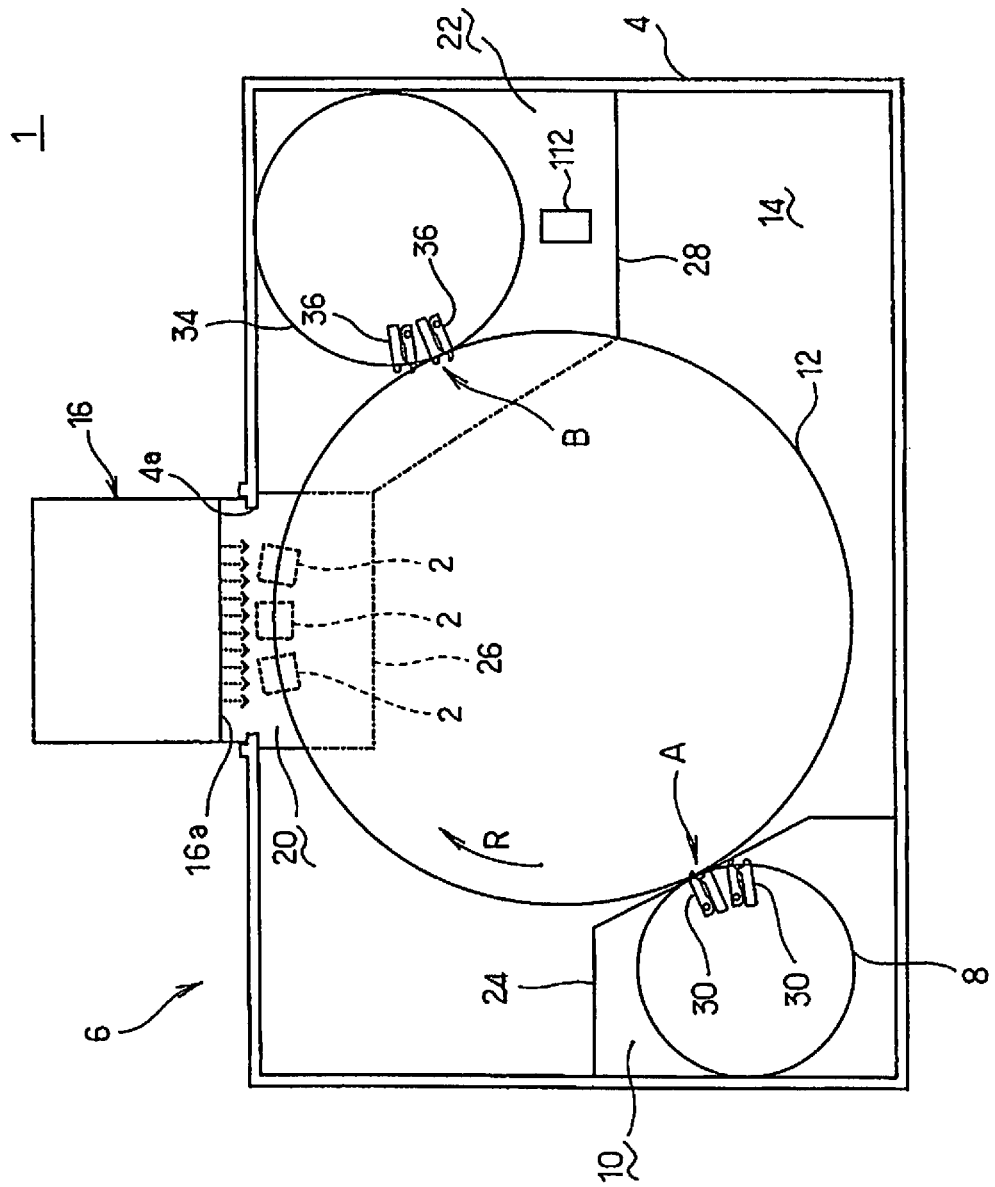
FIG. 1 is a plan view illustrating an entire arrangement of an electron beam irradiation vessel sterilization apparatus (electron beam sterilizer) according to a first embodiment of the present invention.

Preferred embodiments of the present invention will be described hereunder with reference to the accompanying drawings. Further, it is to be noted that terms "upper", "lower", "right", "left" and like terms are used herein with reference to the illustrations of the drawings or an actual arrangement of an apparatus.

An apparatus for sterilizing a vessel by irradiation with an electron beam (which may be called an electron beam sterilizer or vessel sterilizer) 1 according to a preferred embodiment of the present invention includes a sterilization chamber 6 surrounded by wall sections 4 made of lead so as to prevent electron beams or X-rays from leaking outside at a time when a vessel 2 is irradiated with the electron beam so as to sterilize the same.

The interior space of this sterilization chamber 6 is divided into several sections (i.e., chambers) including: a carry-in chamber 10 positioned on an entrance (inlet) side into which a carry-in wheel 8 is disposed; a main chamber 14 in which a conveyance wheel 12 for rotating and conveying the vessel 2 transferred from the carry-in wheel 8; an irradiation chamber 20 positioned in front of the electron beam radiator 16 and irradiates, with the electron beam, the resin vessel 2 supported and conveyed by a bottle support unit or mechanism 18 (FIG. 2A) provided for the conveyance wheel 12; and a carry-out chamber 22 positioned to be continuous to an exit (outlet) side of the irradiation chamber 20 (FIG. 1) and conveying the resin vessel 2 which has been sterilized by the electron beam irradiation while maintaining an aseptic condition thereof toward the downstream side of the vessel conveying path.

These chambers 10, 14, 20 and 22 are defined by inner wall sections 24, 26 and 28, respectively. Further, these inside wall sections 24, 26 and 28 as well as outer wall sections 4 are formed with openings each having a size through which the resin vessel 2 can be transferred through these openings, respectively.

In this embodiment, the vessel sterilized by the electron beam irradiation sterilizer 1 and filled up with an inner content such as liquid in the following processes performed on the downstream side thereof is a resin vessel such as PET bottle 2. This resin vessel 2 has a shell (body) portion having a substantially quadrangular cross-section, as simply illustrated in FIG. 1, and also is provided with a tubular mouth portion 2a at an upper portion of the shell portion. The resin vessel 2 as a PET bottle is further provided with a flanged portion 2b positioned below the mouth portion 2a in a standing state. The resin vessel 2 is conveyed in a suspended state such that an upper or a lower portion of this flanged portion 2b is held by a gripper, or a lower surface side of this flanged portion 2b is supported by the bottle support unit 18 or other support means.

The resin vessels 2 are continuously conveyed by an air conveyer, not shown, are then separated at a predetermined interval by an infeed screw or like, and thereafter, are conveyed into the carry-in chamber 10 disposed on the entrance side of the sterilization chamber 6.

The carry-in wheel 8 disposed in the carry-in chamber 10 is provided with a plurality of grippers 30 arranged along the circumferential direction at an equal interval from each other, and each of the grippers 30 grips the upper portion of the resin vessel 2 above the flanged portion 2b thereof, which is then conveyed in the gripped state.

The conveyance wheel 12 disposed in the main chamber 14 is provided with a plurality of bottle support units (mechanism) 18 along the circumferential direction at an equal interval from each other, and each of the support units 18 supports the lower surface side of the flanged portion 2b of the resin vessel 2, which is then conveyed. The carry-in wheel 8 and the conveyance wheel 12 are synchronously rotated, and the resin vessels 2 are transferred, at a transferring position "A", to the respective bottle support units 18 of the conveyance wheel 12 from the respective grippers 30 of the carry-in wheel 8.

Each of the resin vessels 2 is supported by the bottle support unit 18 of the conveyance wheel 12 and then rotated and conveyed inside the irradiation chamber 20 during which the resin vessel 2 is subjected to the irradiation with the electron beam from the electron beam irradiator 16 entirely along the longitudinal (vertical) direction thereof, thus being sterilized.

The thus sterilized resin vessel 2 is conveyed into the carry-out chamber 22 disposed continuously to the irradiation chamber 20 and transferred to the carry-out wheel 34. A plurality of grippers 36 are arranged on the outer periphery of the carry-out wheel 34 along the circumferential direction at an equal interval from each other, and each of these grippers 36 grips the upper portion of the resin vessel 2 above the flanged portion thereof held by the bottle support unit 18 of the conveyance wheel 12 so as to receive the resin vessel.

The carry-out wheel 34 is also synchronously rotated with the conveyance wheel 12, and at the transferring position "B", the resin vessel 2 is transferred to the gripper 36 of the respective carry-out wheel 34 from each of the respective bottle support unit 18 of the conveyance wheel 12. The resin vessel 2 gripped by the gripper 34 of the carry-out wheel 34 is transferred to a vessel support means disposed in a chamber, not shown, adjacent to the carry-out chamber 22 so as to be subjected to the next process.

As mentioned hereinbefore, the wall section 4 is formed with the opening 4a at a portion corresponding to the irradiation chamber 20, and the electron beam irradiator (irradiation device) 16 is mounted to this opening 4a. This electron beam irradiator 16 is provided with a vacuum chamber (acceleration chamber), not shown, for irradiating the resin vessel with the electron beam, and as is known, a filament is heated in a vacuum state in this vacuum chamber to generate thermal electrons, which are then accelerated by high voltage to generate a high speed electron beam, and the generated electron beam is taken out into the atmosphere through a metallic window foil, such as Ti, attached to an irradiation window 16a of the electron beam irradiator 16 and then irradiates an object to be treated (resin vessel 2 in this embodiment) to thereby perform the sterilization process or like process.

Further, although not shown in FIG. 1, a beam shield 38 (FIG. 2A) is disposed behind the resin vessel 2 subjected to the electron beam irradiation from the electron beam irradiator 16.

In the following, constructions or structures of the bottle support units or mechanisms 18 provided for the conveyance wheel 12 and a ground electrode to be inserted into the resin vessel 2 at the sterilization process will be briefly described with reference to FIGS. 2A and 2B.

The conveyance wheel 12 is composed of a horizontal disk-shaped plate 40, an annular rotational plate 41 fixed to the outer periphery of the disk-shaped plate 40, and an annular intermediate plate 42 disposed above the rotational plate 41 to be integrally rotatable with the rotational plate 41.

A cylindrical rotating shaft 44 disposed in a perpendicular orientation supports the outer peripheries of the rotational plate 41 and the annular intermediate plate 42 to be rotatable through ball bearings 46 and 48, respectively, at an equal interval in the circumferential direction.

A horizontal mount member 50 is fixed to the lower end portion of the cylindrical rotating shaft 44. A pair of gripping members 52A, 52B (which are disposed on the front and rear side on the drawing paper of FIG. 2A) are disposed on the lower side of the mount member 50 so that the resin vessel 2 can be held directly below the cylindrical rotating shaft 44.

In the bottle support unit 18, the paired gripping members 52A, 52B are mounted to the lower end portions of a pair of leaf (plate) springs 54A, 54B so as to hold the resin vessel by the urging force of the leaf springs 54A, 54B.

A pinion gear 64 is fixed to the upper end portion of the cylindrical rotating shaft 44, to which the bottle support unit 18 is mounted, projecting over the intermediate plate 42. Furthermore, a vertically extending intermediate shaft 66 is supported to be rotatable through ball bearings 68 and 70 at a portion radially inside of a position at which the cylindrical shaft 44 is supported, of the annular rotational plate 41 and the annular intermediate plate 42 fixed to the outer periphery of the disk-shaped plate 40. A sector gear 72 is mounted to the upper end portion of the intermediate shaft 66 at a level substantially equal to that of the pinion gear 64 of the rotational shaft 44. The sector gear 72 is formed with teeth facing radially outward of the conveyance wheel 12 so as to be meshed with the pinion gear 64.

Incidentally, a perpendicular pin 74 is attached to an end portion (left end in FIG. 2A) directing radially inward of the conveyance wheel 12 so as to penetrate the sector gear 72, and a cam follower 76 is supported to an upper end portion of the perpendicular pin 74 to be rotatable. A tension coil spring 80 is interposed between the lower end portion of the perpendicular pin 74 and a spring receiving pin 78 fixed to an inner peripheral end of the intermediate plate 42 so as to attract the end portion of the sector gear 72 toward the radially inside of the conveyance wheel 12.

A circular stationary plate 82 is disposed above the disk-shaped plate 40 of the conveyance wheel 12, and a cam 84 for swinging the sector gear 72 is fixed to the outer periphery of the circular stationary plate 82. An outer peripheral surface of this cam 84 is formed as a cam surface, along which the cam follower 76 moves while rotating. According to the swinging motion in the radial direction due to the rotational movement of the cam follower 76, the sector gear 72 is rotated around the intermediate shaft 66 to thereby rotate the pinion gear 64.

The bottle support unit 18 is mounted to the lower end portion of the cylindrical rotating shaft 44 to the upper end of which the pinion gear 64 is fixed. Then, when the pinion gear 64 is rotated by the swinging motion of the sector gear 72, and the cylindrical rotating shaft 44 disposed above the mouth portion 2a of the resin vessel 2 is rotated, so that the resin vessel 2 supported and conveyed by the bottle support unit 18 is rotated with its gravity (own weight) axis being the center of the rotation. In this embodiment, the pinion gear 64 is rotated by the rotation of the sector gear 72 so as to rotate the resin vessel 2 in the forward and reverse direction by about 180 degrees.

The mount member 50, mentioned hereinbefore, is formed with a through hole 50a at a position vertically corresponding to an inner hole 44a of the cylindrical rotating shaft 44. Further, a ceiling surface and an outer peripheral surface of the conveyance wheel 12 are covered by a cover 88, and the upper portion of the pinion gear 64 reaches the cover 88 covering the ceiling surface of the conveyance wheel 12 so as to seal a portion between the cover 88 and the upper portion of the pinion gear 64 in a slidable manner. According to such a structure as mentioned above, circular holes 44a of the rotating shaft 44 and a circular hole 64a of the pinion gear 64 vertically penetrate the inside space surrounded by the disk-shaped plate 40 and the cover 88 to thereby shut off the internal environment surrounded by the disk-shaped plate 40 and the cover 88 from an ambient environment maintained in an aseptic state.

Figure 2:
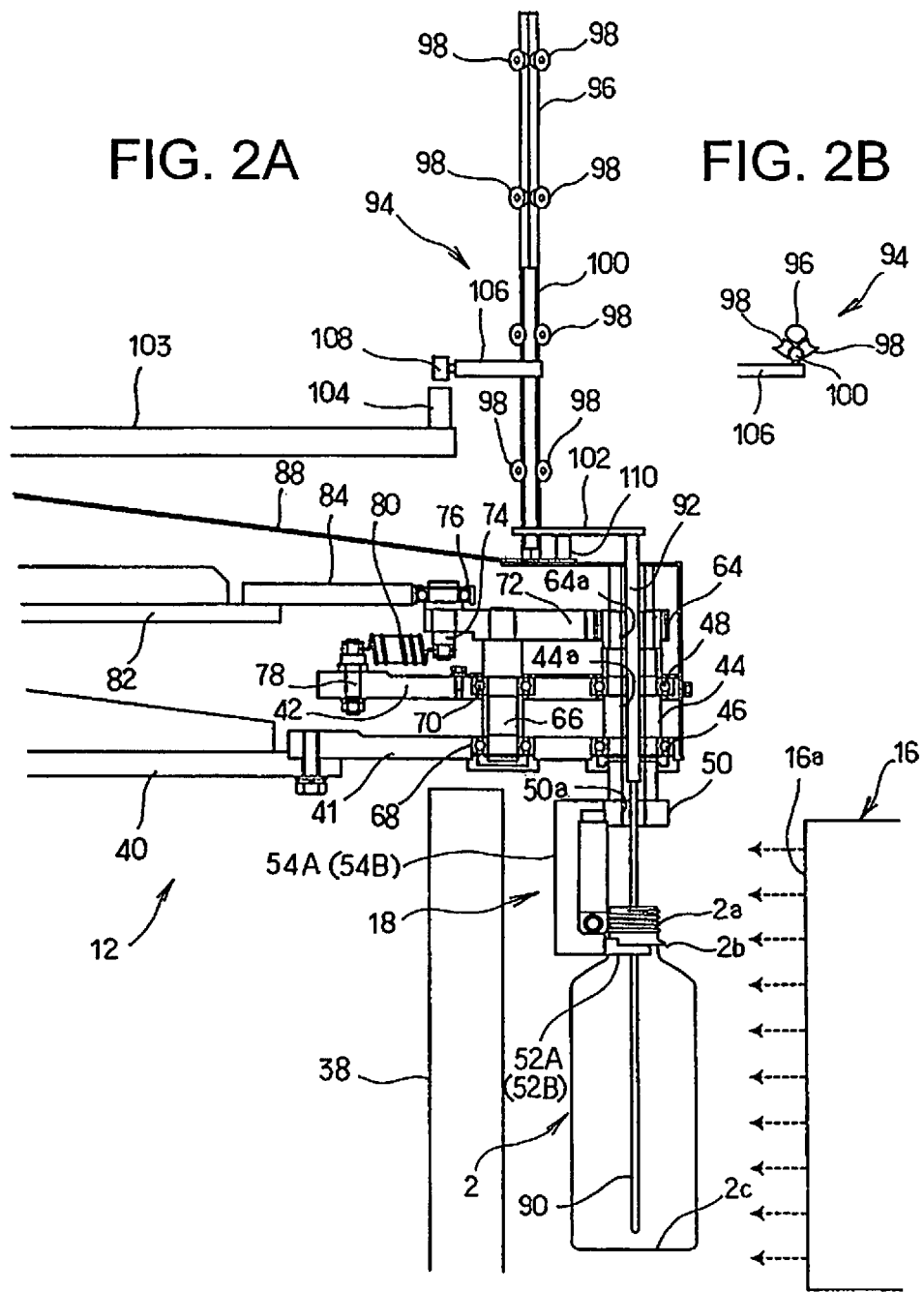
FIG. 2A is an illustrated elevational section showing an essential portion of a conveying wheel provided with a bottle holding unit.
FIG. 2B is a plan view illustrating a mechanism for elevating a ground electrode.
Figure 3:
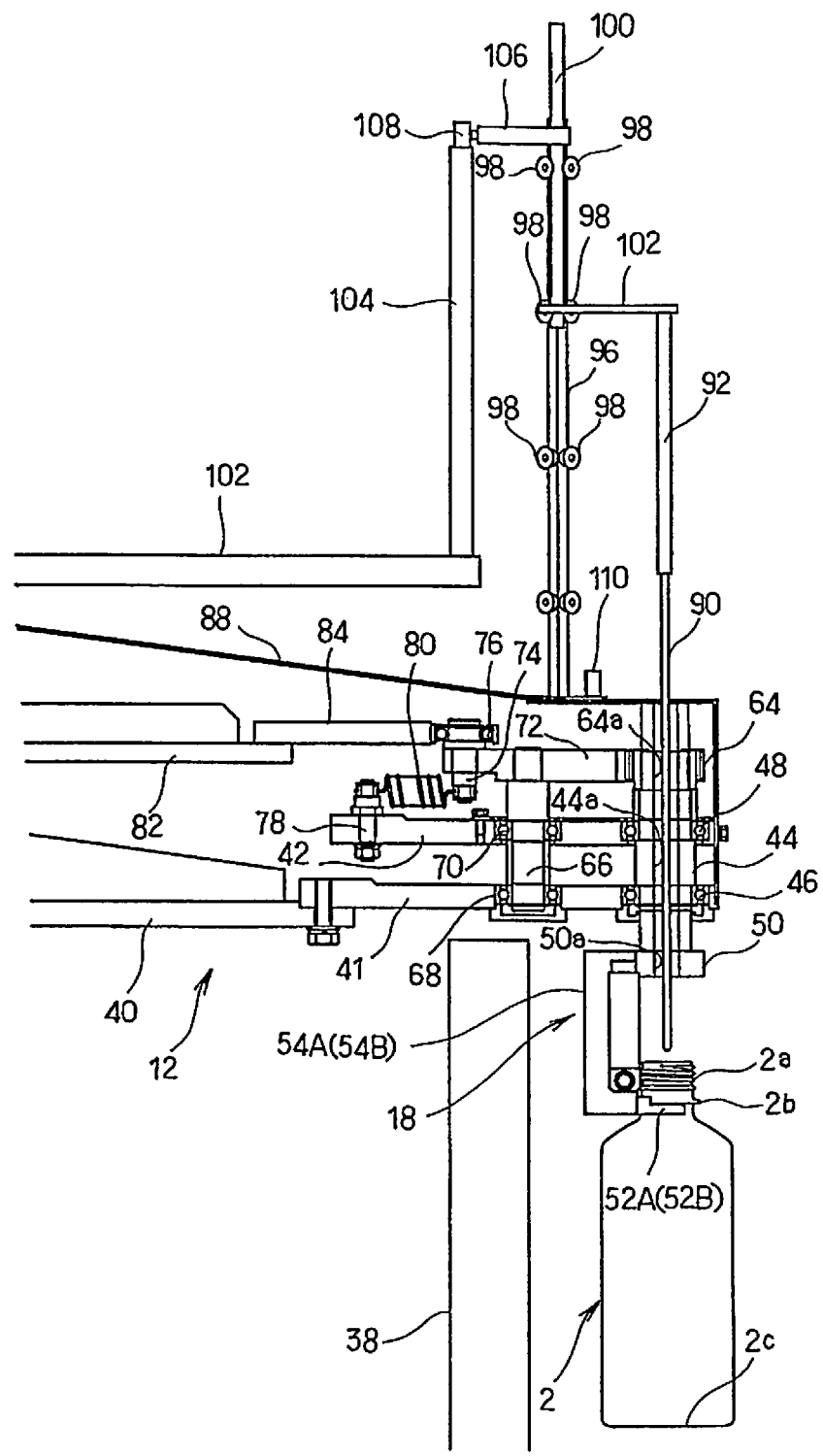
FIG. 3 is an enlarged view showing a state other than irradiation with an electron beam in FIG. 2A.

As shown in FIG. 2A, FIG. 2B or FIG. 3, the conveyance wheel 12 is provided with a ground electrode 90 which is inserted into the resin vessel 2, when the resin vessel 2 being conveyed by the bottle support unit 18 is irradiated with the electron beam. The ground electrode 90 is attached to a lower end portion of a vertically extending support rod 92 in a manner such that the ground electrode 90 and the support rod 92 elevate so as to penetrate the circular hole 44a of the cylindrical rotating shaft 44 and the circular hole 64a of the pinion gear 64 fixed to the upper portion of the shaft 44 and also penetrate the through hole 50a of the horizontal mount member 50 disposed below.

Hereunder, a structure or mechanism for carrying out the elevational motion of the ground electrode 90 will be explained.

A guide mechanism 94 is disposed in a vertically extending fashion at a radially inside position to which the cylindrical rotating shaft 44 is positioned above the cover 88. This guide mechanism 94 is, as shown in FIGS. 2A and 2B, provided with a vertically extending guide member 96 and a plurality of guide rollers 98 mounted to a plurality of vertical portions of the guide member 96. These guide rollers 98 are arranged in pairs at vertically appropriate portions of the guide member 96, and an elevating rod 100 is elevated vertically in a manner supported by the guide rollers 98 and the guide member 96. The support rod 92 and the ground electrode 90, mentioned hereinabove, are mounted to the lower end portion of the elevating rod 100 through a horizontal mount member 102 so as to vertically elevate the ground electrode 90 in accordance with the elevating motion of the elevating rod 100.

This ground electrode 90 may be formed of a metal material such as stainless steel, aluminium, titanium, or like, or other electrically conductive materials. Furthermore, the ground electrode 90 may have a round rod shape, or other shape having a rectangular, oblong or polygonal section, and moreover, it may be formed so as to provide a saw-tooth shape provided with a number of projections or brushes on its outer peripheral surface so as to smoothly induce electric charges.

A horizontally arranged stationary member 103 is disposed above the ceiling surface of the cover 88 independent from the conveyance wheel 12, and an elevating cam 104 is attached to the outer peripheral portion of the stationary member 103.

Incidentally, an elevational member 106 arranged horizontally is fixed to the elevating rod 100 at a position higher than the location of the mount member 102, and a cam follower 108 is attached to a distal (front) end portion of this elevational member 106. This cam follower 108 rolls and moves on the upper surface (cam surface) of the elevating cam 104 so as to carry out elevating motion following the cam shape to thereby elevate the ground electrode 90. When the cam follower 108 is pushed upward to the highest position by the elevating cam 104, the lower end of the ground electrode 90 takes a position above the mouth portion 2a of the resin vessel 2 (FIG. 3), and on the other hand, when the cam follower 108 is lowered downward, the lower end of the ground electrode 90 is inserted into the vessel 2 to take a position near the bottom surface 2c of the resin vessel 2. Further, at this time, the lowered end of the elevating rod 100 is restricted in its downward movement by the abutment of the horizontal mount member 102 against a support member 110 fixed to the ceiling surface of the cover 88, and the cam follower 108 stops at a height level not contacting the cam surface of the elevating cam 104. In this positional condition, the ground electrode 90 becomes conductive to the cover 88 made of metal material through the support rod 92, the mount member 102 and the support member 110, which are all formed of conductive metal materials, to thereby create a conductive condition between the ground electrode 90 and the cover 88, and thus, the electric charges flow from the ground electrode 90 toward the cover 88.

After the resin vessel 2 supported and conveyed by the bottle support unit 18 of the conveyance wheel 12 has been sterilized by the irradiation with the electron beam from the electron beam irradiator 16, the resin vessel 2 is transferred to the gripper 36 of the carry-out wheel 34 and then rotated and conveyed.

Figure 4:
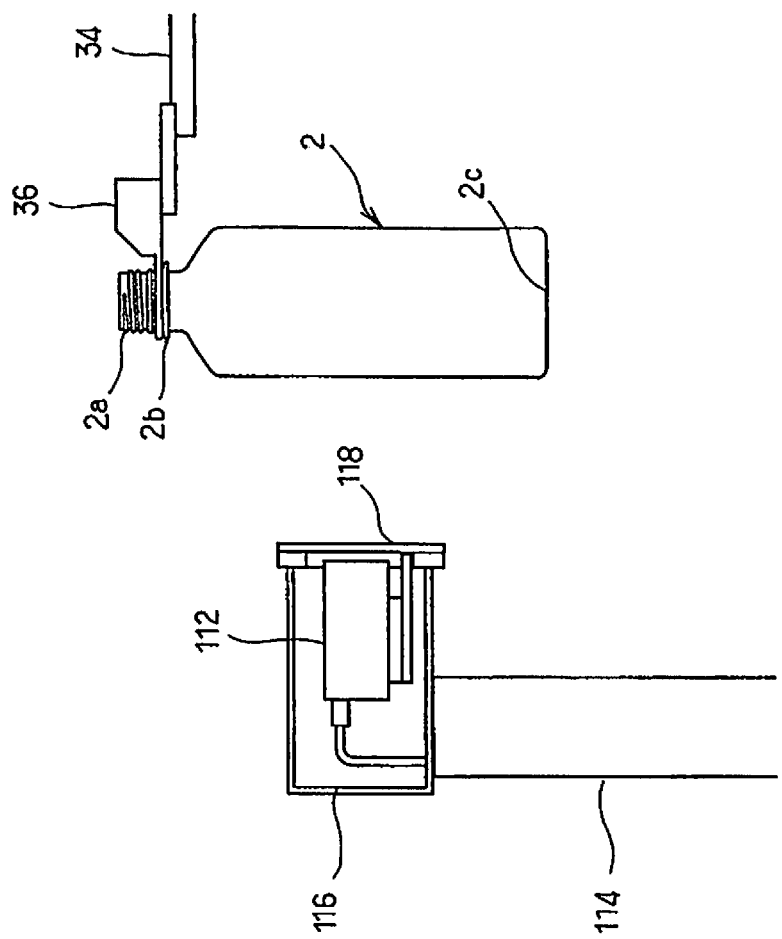
FIG. 4 is a view explaining an ionizer provided for the conveying wheel.

A soft X-ray type ionizer 112 as a charge-removing means is arranged outside the vessel conveying path provided with the gripper 6 of the carry-out wheel 34 (refer to FIG. 1 or 4). Since the structure of such a soft X-ray type ionizer 112 is well known in the art, explanation thereof will be omitted herein (for example, see Patent Publication 2). In this embodiment, the soft X-ray ionizer 112 is accommodated within an accommodation case 116 fixed onto a column 114. The soft X-ray ionizer 112 has a front surface side from which a soft X-ray is emitted, and this front surface is covered by a soft X-ray permeable resin film 118.

In the electron beam irradiation vessel sterilization apparatus (electron beam sterilizer) 1 of this embodiment, since the interior of the sterilization chamber 6 is sterilized by a medical agent (medicine), the soft X-ray ionizer 112 is accommodated within the case 116 and is sealed with the resin film 118 to thereby prevent the medicine from adhering to the ionizer 112. Note that the charge-removing means may be arranged above or below the conveying resin vessel without being limited to the shown arrangement on the side position thereof.

The operation and function of the electron beam sterilizer 1 of the structures mentioned above will be described hereunder.

The resin vessels 2 sterilized by the electron beam sterilizer 1 according to this embodiment are conveyed by a neck conveyer, not shown, and separated by a predetermined pitch, respectively. Thereafter, the resin vessels 2 are conveyed by a conveying wheel, not shown, into the carry-in chamber 10 in the aseptic chamber 6 surrounded by the wall sections 4 made of lead. The carry-in wheel 8 disposed within the carry-in chamber 10 is provided with a plurality of grippers 30 arranged in the circumferential direction at an equal interval from each other, and these grippers grip the upper side portions of the flanged portions 2b positioned on the lower side of the tubular mouth portions 2a of the respective resin vessels 2. The resin vessels 2 gripped and held by the grippers 30 are rotated and conveyed by the rotation of the carry-in wheel 8 to the position "A" at which the resin vessels 2 are transferred to the bottle support units 18 provided for the conveyance wheel 12 from the grippers 30 of the carry-in wheel 8, respectively.

The bottle support unit 18 is rotated and moved in a manner such that one of the grip members 52A, 52B is directed forward in the rotating direction and the other one thereof is directed rearward in the rotating direction, and at the transferring position "A", the mouth portion 2a of the resin vessel 2 gripped by the gripper of the carry-in wheel 8 is pushed into a space between both the grip members 52A and 52B.

Both the grip members 52A, 52B are mounted to the lower end portions of the leaf springs 54A, 54B, respectively, and the space between the gripper members 52A and 52B are opened by forcibly pushing the mouth portion 2a of the resin vessel 2 into the space therebetween so as to grip the same. Thereafter, both the leaf springs 54A and 54B return to their original positions by their own spring force, and then, as shown in FIGS. 2A and 2B, hold the lower side of the flanged portion 2b of the resin vessel 2 as well as support the lower surface thereof.

According to the rotation of the conveyance wheel 12, the resin vessels 2 supported respectively by the bottle support units 18 are rotated and conveyed in an arrowed direction "R" in FIG. 1 and enter the electron beam irradiation chamber 20. When each of the resin vessels 2 is subjected to the electron beam irradiation in the irradiation chamber 20, the ground electrode 90 has been lowered by the operation of the elevating cam 104 to the position, as shown in FIG. 2A, till the front end (lower end) thereof almost reaches the bottom surface 2c of the resin vessel 2 from the opening of the mouth portion 2a of the vessel 2. Further, in the sections or portions other than this section now being irradiated with the electron beam, the ground electrodes 90 are lifted upward by the elevating cam 104, and the front ends thereof are positioned above the mouth portions 2a of the resin vessels 2 in the state shown in FIG. 3. As mentioned above, during the movement of the resin vessel 2 into which the ground electrode 90 is inserted in the front side of the irradiation window 16a of the electron beam irradiator 16, the resin vessel 2 is sterilized by the electron beam irradiation.

If the resin vessel 2 into which the ground electrode 90 is not inserted is irradiated with the electron beam, the resin vessel 2 is charged with electrons. However, by inserting the ground electrode 90 into the resin vessel 2 at the time of the electron beam irradiation such as in this embodiment, the electrons emitted by the electron beam irradiation penetrate the resin material of the vessel 2 and enter the interior of the resin vessel 2 through the opening of the mouth portion 2a of the vessel 2. Then, the electrons are induced by the ground electrode 90 and flow entirely of the apparatus from the cover 88 through the support rod 92, the mount member 102 and the support member 110, and accordingly, the charging on the inner surface of the resin vessel 2 and interior of the resin material of the vessel 2 can be effectively prevented. Especially, the electrons emitted toward the outer surface of the resin vessel 2 act so as to permeate the resin material not only by the penetrating force by the acceleration at the electron beam irradiation time but also by the induction of the ground electrode 90 from the inside of the resin vessel 2, thus staying inside the resin material and hence preventing it from being charged.

Further, the pinion gear 64 is fixed to the upper end portion of the cylindrical rotating shaft 44, to which the bottle support unit 18 is attached, and is meshed with the sector gear 72, which is engaged with the cam 84 mounted to the outer periphery of the stationary plate 82 to be swingable. During the movement of the cylindrical rotating shaft 44 in front of the electron beam irradiator 16 by the operation of the cam 84, the cylindrical rotating shaft 44 is rotated to thereby rotate the resin vessel 2 supported by the bottle support unit 18 by 180 degrees in forward and reverse directions. As mentioned above, by the rotation of the resin vessel 2 by 180 degrees in front of the irradiation window 16a of the electron beam irradiator 16, the resin vessel 2 can be irradiated with the electron beam and, hence, sterilized entirely in both the vertical and conveyance directions. The cylindrical rotating shaft 44, the pinion gear 64, the sector gear 72 and the cam 84 constitute a rotating means for rotating the resin vessel 2.

As described above, the ground electrode 90 is inserted into the center portion in the resin vessel 2 and irradiated with the electron beam, so that it is difficult to irradiate the electron beam to the rear side of the ground electrode 90 because of shading in itself. Although the electron beams emitted from the electron beam irradiator go rectilinear as a whole, some measure of these electron beams collide with the resin vessel 2 and an atmospheric molecule. Accordingly, the body portion of the resin vessel having a relatively wide space to the ground electrode 90 can be indirectly irradiated with the electron beam. On the other hand, the neck portion of the resin vessel having a relatively narrow space to the electrode 90 is hardly irradiated with the electron beam to the rear side thereof. Therefore, the rotation of the resin vessel 2 by the above rotating means can make the whole of the resin vessel 2 irradiated with the electron beam effectively.

The resin vessel 2 irradiated and sterilized with the electron beam during the passing inside the irradiation chamber 20 is rotated and conveyed in the state supported by the bottle support unit 18 from the irradiation chamber 20 to the carry-out chamber 22. The carry-out wheel 34 is disposed inside the carry-out chamber 20, and the resin vessel 2 which is supported by the bottle support unit 18 at the lower side of the flanged portion 2b is transferred to the gripper 36 provided for the carry-out wheel 34 so as to grip the upper side of the flanged portion 2b of the resin vessel 2. The resin vessel 2 rotated and conveyed in the state supported by the gripper 36 of the carry-out wheel 34 then reaches the position of the soft X-ray ionizer 112, which acts to ionize the atmosphere around the electrically charged object (resin vessel 2 in this embodiment) by the soft X-ray irradiating energy and neutralize the static electricity. At the time of the electron beam irradiation by the electron beam irradiator 16, the inner surface and the inside of the resin material forming the resin vessel 2 are prevented from being electrically charged by the insertion of the ground electrode 90 into the resin vessel 2, and in addition, the irradiation of the soft X-ray by the soft X-ray ionizer 112 to the resin vessel 2 after the electron beam irradiation can remove the charging on the outer surface of the resin vessel 2.

Figure 5:
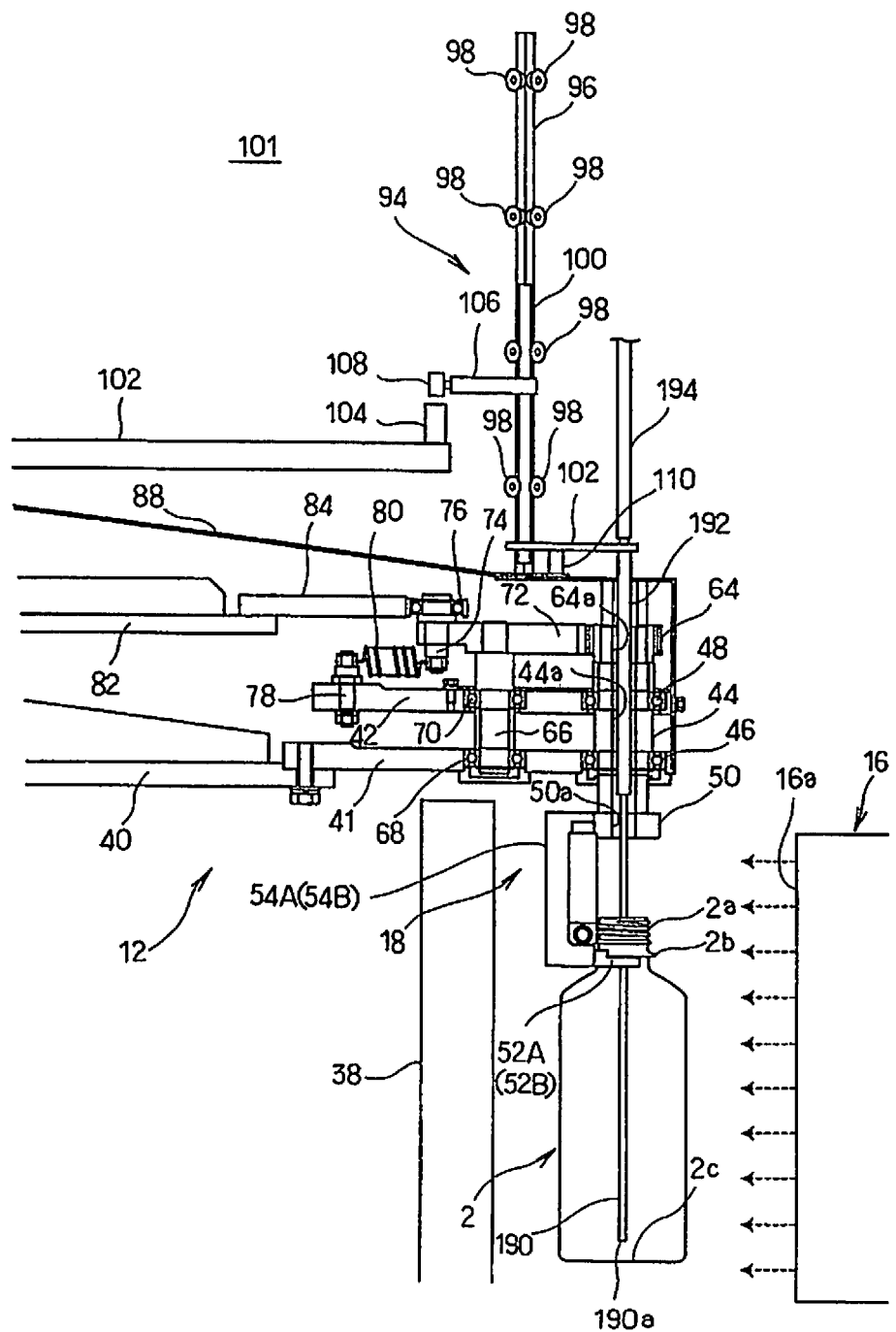
FIG. 5 is an illustrated elevational section, in a state corresponding to FIG. 2A, of an electron beam irradiation vessel sterilization apparatus (electron beam sterilizer) according to a second embodiment of the present invention.

Hereunder, a second embodiment of an electron beam irradiation vessel sterilization apparatus (electron beam sterilizer) 101 will be described with reference to FIG. 5 showing arrangement or structure corresponding to FIG. 2A which represents the first embodiment.

The electron beam sterilizer 101 of this second embodiment has a basic structure similar to that of the first embodiment, and differs in a structure or type a gas passage for blowing an aseptic gas into an interior of the resin vessel 2 at the time of the electron beam irradiation, and therefore, hereunder, only the different structure will be explained, and like reference numerals are added to members and portions corresponding to those of the first embodiment and duplicated description is omitted herein.

In this second embodiment, a ground electrode 190 and a support rod 192 disposed above the ground electrode 190 have hollow structures so as to form gas passages through which a gas flows.

In addition, an aseptic gas supply source, not shown, provided with an aseptic filter such as a HEPA filter is connected to an upper end portion of the support rod 192. In this embodiment, when the resin vessel 2 is sterilized by the electron beam irradiation from the electron beam irradiator 16, as in the first embodiment, the ground electrode 190 has been inserted into the resin vessel 2, and during the irradiation of the electron beam, a gas such as air or an inactive gas such as nitrogen or argon passing through the aseptic filter blows out from a blow-out port 190a formed to the front end of the ground electrode 190 into the resin vessel 2.

As mentioned above, by performing the electron beam irradiation while blowing out the aseptic gas to a portion near the bottom portion of the resin vessel 2, ozone generated by the electron beam irradiation is pushed out and removed from the opening of the mouth portion 2a of the vessel 2 as well as dirt and dust, thus effectively performing an air-rinsing effect. Particularly, when the inactive gas is utilized, since the oxygen density inside the resin vessel 2 is lowered, the effect of preventing the ozone generation can be further improved, and in addition, the aseptic gas does not reduce the sterilization effect. Still furthermore, by blowing out the aseptic gas ionized by an ionizing device, the electrical charging on the inside surface of the resin vessel 2 can be further prevented in addition to the function of the ground electrode 190 itself. In such occasion, since the resin vessel 2 is negatively charged by the irradiation of the electron beam, in order to neutralize this state, the blow-out of positive ion may be effective. Furthermore, the irradiation of the electron beam generates nitrogen oxide, which will dissolve into the water content in the air and may generate nitric acid, and since nitric acid corrodes the apparatus, in order to prevent such an adverse phenomenon, it is desirable to blow out sufficiently dried dry aseptic gas.

In the embodiments described above, the resin vessel 2 is irradiated with the electron beam in the state in which the ground electrode 90 or 190 is inserted into the resin vessel 2, and the emitted electrons flow from the ground electrode 90 or 190 toward the cover 88. However, the present invention is not limited to such embodiments.

Figure 6:
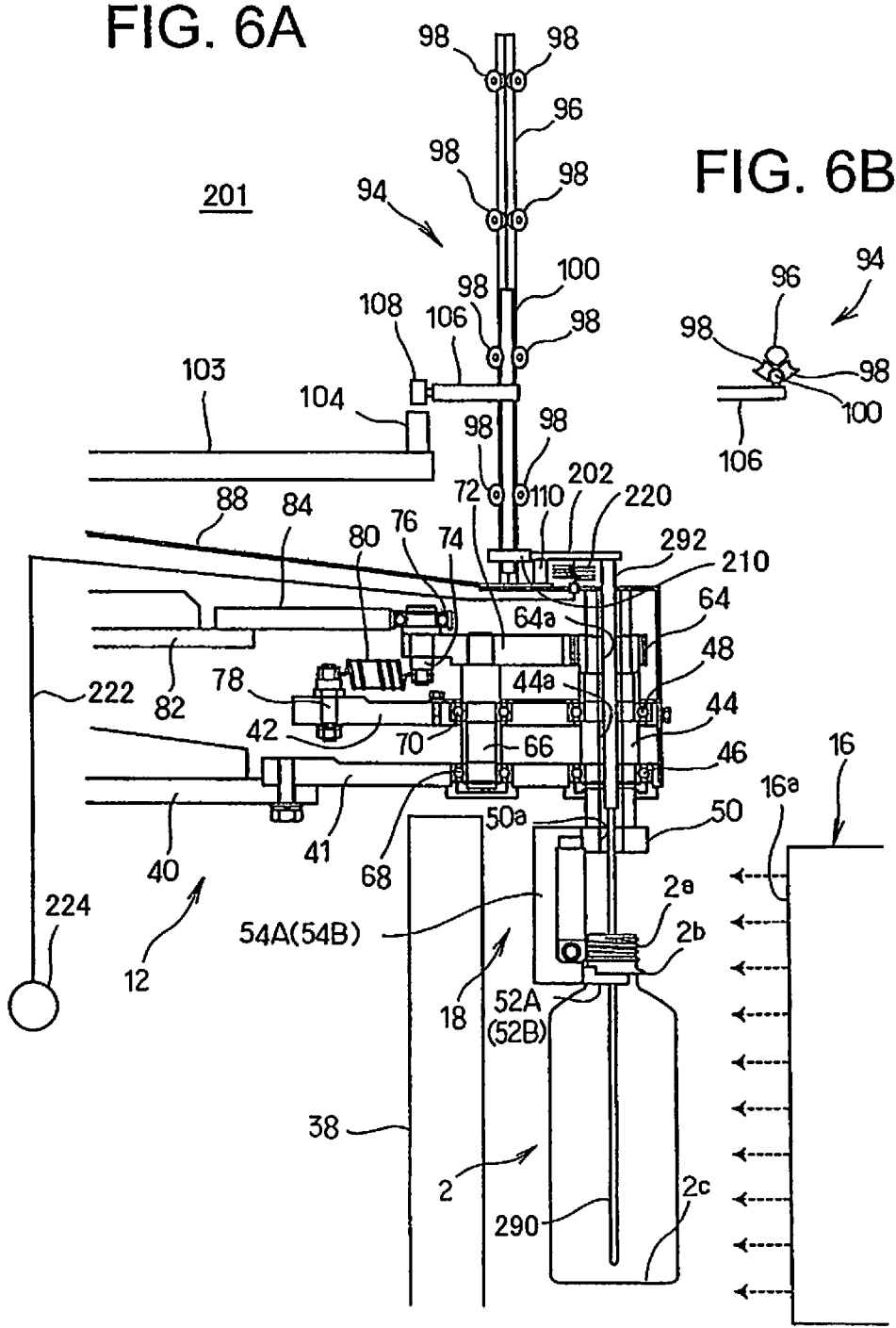

FIGS. 6A and 6B are an elevational section of an essential portion of an electron beam irradiation vessel sterilization apparatus (electron beam sterilizer) 201 according to a third embodiment of the present invention. This third embodiment differs from the aforementioned embodiments in the structure of a member to be inserted into the resin vessel at the time of the electron beam irradiation, and like reference numerals are added to members and portions corresponding to those of the first or second embodiment and duplicated description is omitted herein.

In this third embodiment, the carry-in wheel 12 is provided with an insertion member (positive potential rod) to be inserted into the interior of the resin vessel 2 at the time of the electron beam irradiation to the resin vessel 2 being conveyed by the bottle support unit 18.

The positive potential rod 290 is attached to the lower end portion of a vertically arranged support rod 292, and the positive potential rod 290 and the support rod 292 are arranged so as to penetrate and elevate the cylindrical rotating shaft 44, pinion gear 64 fixed to the upper end thereof, the circular holes 44a and 64a, and the through hole 50a of the horizontal mount member 50 disposed below.

A structure for elevating the positive potential rod 290 will be described hereunder.

As shown in FIG. 6A, the vertically extending guide mechanism 94 is disposed radially inside of the location of the cylindrical rotating shaft 44 above the cover 88. This guide mechanism 94 shown in FIGS. 6A and 6B has substantially the same structure of that of the first embodiment shown in FIGS. 2A and 2B. A horizontal mount plate 202 is fixed to the lower end portion of the elevating rod 100 of the guide mechanism 94 through an insulating member 210, and the support rod 292 and the positive potential rod 290 are attached through the horizontal mount plate 202 so that the positive potential rod 290 is elevated by the elevating motion of the elevating rod 100. Further, the positive potential rod 290 may be made of an electrically conductive substance or metal such as stainless steel, aluminium, titanium or the like, or other conductive material. Furthermore, the positive potential rod 290 may have a shape such as a round shape, or rectangular shape, oblong shape or polygonal shape in section, or a sawtooth shape having a number of projections formed on an outer periphery thereof, or a shape provided with brush, which will readily provide a charge induction function.

Figure 7:
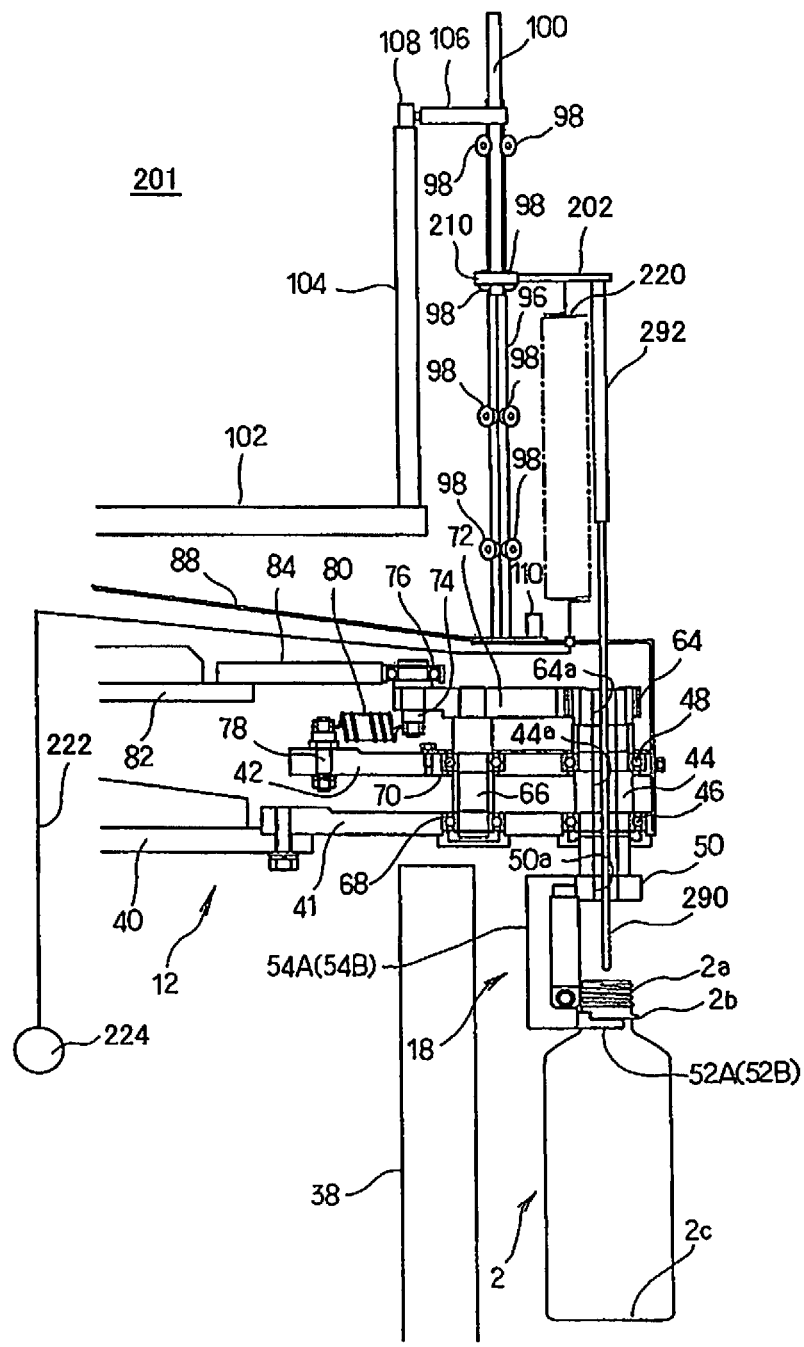
FIG. 7 is a view showing a state other than irradiation with an electron beam in FIG. 6A.

When the cam follower 108 of the guide mechanism 94 is pushed upward to the uppermost position by the elevating cam 104, the lower end portion of the positive potential rod 290 takes a position above the mouth portion 2a of the resin vessel 2 as shown in FIG. 7, and on the other hand, when the cam follower 108 is pushed downward to the lowermost position, the lower end portion of the positive potential rod 290 is inserted into a portion near the bottom surface 2c of the resin vessel 2.

The positive potential rod 290 is operatively connected to a positive electrode 224, to which a positive potential is applied, through the upper support rod 292, the horizontal mount member 202, an expansion coil 220 disposed between the lower surface of the mount member 202 and the cover 88, and a conductive wire 222. The positive potential is always applied to this positive electrode 224 during the operation of the apparatus, and since the insertion member 290 is in a state applied with the positive potential, this insertion member 290 is called "positive potential rod 290" herein with respect to this embodiment.

Next, the operation of the electron beam irradiation vessel sterilization apparatus (electron beam sterilizer) according to this embodiment will be described.

According to the rotation of the conveyance wheel 12, the resin vessel 2 supported by the bottle support unit 18 enters the electron beam irradiation chamber 20 in which the resin vessel 2 is subjected to the electron beam irradiation. When the resin vessel 2 is irradiated with the electron beam in this irradiation chamber 20, the positive potential rod 290 has been lowered by the operation of the elevating cam 104, and as shown in FIG. 6A, the front end (lower end) of the rod 290 is inserted into a position of the level near the bottom surface 2c of the resin vessel 2 through the opening of the mouth portion 2a thereof.

Further, in the sections or areas other than that in which the resin vessel 2 is irradiated with the electron beam, the positive potential rods 290 are elevated upward by the elevating cams 104 such that the front (lower) ends of the potential rods 290 are positioned above the openings of the mouth portions 2a of the resin vessels 2, respectively, in the state shown in FIG. 7. In the manner mentioned above, the resin vessel 2, into which the positive potential rod 290 is inserted, is irradiated with the electron beam during the passing in front of the irradiation window 16a of the electron beam irradiator 16, thus being sterilized. On the other hand, if the resin vessel 2, into which the positive potential rod 290 is not inserted, is irradiated with the electron beam, the resin vessel 2 will be charged with electrons. However, as in this embodiment, by inserting the positive potential rod 290 into the resin vessel 2 at the time of the electron beam irradiation, the emitted electrons penetrate or permeate inside the resin material of the resin vessel 2 and enter the resin vessel 2 through the opening of the mouth portion 2a of the resin vessel 2, and then, the electrons flow by the induction of the positive potential rod 290. Accordingly, the inner surface of the resin vessel 2 and the interior of the resin material forming the vessel 2 can be prevented from being electrically charged. Particularly, the electrons emitted toward the outer surface of the resin vessel 2 penetrate or permeate the resin material not only by the penetration force due to acceleration at the time of the electron beam irradiation but also by the induction to the positive potential rod 290 from the inside of the resin vessel 2, whereby the electrons stay inside the resin material and, thus, the resin vessel 2 is prevented from being electrically charged.

Further, it is to be noted that, although, in the described embodiment, the insertion member 290 is connected to a positive electrode so as to provide positive potential, it is always not necessary to be connected to the positive electrode, and it may be possible to preliminarily charge the insertion member 290 with positive electric charges. For example, it may be possible to generate static electricity to the insertion member 290 by friction to create a positively charged state, and in such case, an effect substantially identical to that obtained in the case of the connection of the positive electrode is obtainable. In the case where the insertion member 290 is connected to the positive electrode, the electrons flow outside the resin vessel 2 through the insertion member 290, but in the case where the insertion member 290 is preliminarily charged, the electrons may be attracted to the positive charges.

Furthermore, in this embodiment, as like as the second embodiment, it may be possible to form a gas passage through which the gas flows in the interiors of the positive potential rod 290 and the support rod 292 disposed above the potential rod 290, to connect the gas passage to an aseptic gas supply source provided with an aseptic filter such as HEPA filter and to blow out, from the front end of the positive potential rod 290, the gas composed of air or an inactive gas such as nitrogen or argon passing through the aseptic filter from the positive potential rod 290 inserted into the resin vessel 2 during the electron beam irradiation. In this case, substantially the same effects as those attained by the second embodiment may be attained.

It is further to be noted that the present invention is not limited to the described embodiments and many other changes and modifications may be made, such as those mentioned above, without departing from the scope of the appended claims.

What is claimed is:

1. An electron beam sterilization method for sterilizing a resin vessel which is transferred by a transfer means by irradiating the resin vessel with electron beam emitted from an electron beam irradiator, wherein inserting a ground electrode into an interior of the resin vessel through an opening thereof by an insert means and, in this state, irradiating the resin vessel with the electron beam by an electron beam irradiator, and effectively preventing electrons from remaining inside the wall of the resin vessel.

2. The method of claim 1, additionally comprising the step of blowing an aseptic gas into the resin vessel through a gas passage provided in the ground electrode during the irradiation of the resin vessel.

3. An electron beam sterilization method for sterilizing a resin vessel which is transferred by a transfer means by irradiating the resin vessel with electron beam emitted from an electron beam irradiator, wherein inserting an insertion member having a positive potential into an interior of the resin vessel through an opening thereof by an insert means and, in this state, irradiating the resin vessel with the electron beam by an electron beam irradiator, and effectively preventing electrons from remaining inside the wall of the resin vessel.

4. The method of claim 3, additionally comprising the step of blowing an aseptic gas into the resin vessel through a gas passage provided in the insertion member during the irradiation of the resin vessel.

\* \* \* \* \*